United States Patent
Timken et al.

(10) Patent No.: US 10,301,233 B2
(45) Date of Patent: May 28, 2019

(54) NATURAL GAS LIQUID UPGRADING BY IONIC LIQUID CATALYZED ALKYLATION

(71) Applicant: Chevron U.S.A. Inc., San Ramon, CA (US)

(72) Inventors: Hye-Kyung Cho Timken, Albany, CA (US); Kenneth John Peinado, Antioch, CA (US); Bong-Kyu Chang, Novato, CA (US)

(73) Assignee: Chevron U.S.A. Inc., San Ramon, CA (US)

( * ) Notice: Subject to any disclaimer, the term of this patent is extended or adjusted under 35 U.S.C. 154(b) by 0 days.

(21) Appl. No.: 15/640,655

(22) Filed: Jul. 3, 2017

(65) Prior Publication Data

US 2019/0002368 A1  Jan. 3, 2019

(51) Int. Cl.
| | | |
|---|---|---|
| C07C 2/54 | (2006.01) | |
| C07C 2/58 | (2006.01) | |
| C07C 5/333 | (2006.01) | |
| B01J 31/02 | (2006.01) | |
| C10G 29/20 | (2006.01) | |
| C10G 57/00 | (2006.01) | |
| C10G 5/00 | (2006.01) | |
| C10G 9/00 | (2006.01) | |

(52) U.S. Cl.
CPC .............. *C07C 2/58* (2013.01); *B01J 31/0284* (2013.01); *C07C 5/3335* (2013.01); *C07C 5/3337* (2013.01); *C10G 5/00* (2013.01); *C10G 9/00* (2013.01); *C10G 29/205* (2013.01); *C10G 57/005* (2013.01); *C07C 2521/04* (2013.01); *C07C 2521/18* (2013.01); *C07C 2523/26* (2013.01); *C07C 2523/42* (2013.01); *C07C 2531/02* (2013.01)

(58) Field of Classification Search
CPC ........................................................ C07C 2/58
USPC .................................................. 585/331, 709
See application file for complete search history.

(56) References Cited

U.S. PATENT DOCUMENTS

| | | |
|---|---|---|
| 2,317,901 A | 4/1943 | Frey |
| 2,366,716 A | 1/1945 | Frey |

(Continued)

FOREIGN PATENT DOCUMENTS

WO  2018044406 A1  3/2018

OTHER PUBLICATIONS

"Hydraulic fracturing market projected to continue growth", Oil & Gas Financial Journal (2015), pp. 1 and 2 (Year: 2015).*

(Continued)

*Primary Examiner* — Philip Y Louie
*Assistant Examiner* — Aaron W Pierpont
(74) *Attorney, Agent, or Firm* — Susan M. Abernathy; Terrence M. Flaherty

(57) ABSTRACT

We provide a process, comprising:
a. dehydrogenating natural gas liquid to produce a mixture comprising olefins and unconverted paraffins;
b. without further purification or modification other than mixing with an isoparaffin, sending the mixture to a single alkylation reactor;
c. alkylating the olefins with the isoparaffin, using an ionic liquid catalyst, to produce one or more alkylate products; and
d. distilling the one or more alkylate products and collecting a bottoms distillation fraction that is a middle distillate blending component having a sulfur level of 50 wppm or less and a Bromine number less than 1.

12 Claims, 4 Drawing Sheets

Natural Gas Liquid ($C_5 - C_6$) Upgrading to Alkylate Jet or Diesel

(56) References Cited

U.S. PATENT DOCUMENTS

| | | | |
|---|---|---|---|
| 2,376,077 A | 5/1945 | Oberfell | |
| 2,385,806 A | 10/1945 | Foster | |
| 3,660,272 A | 5/1972 | Frick | |
| 4,367,357 A * | 1/1983 | Vora | C07C 9/16 585/314 |
| 4,429,173 A * | 1/1984 | Hutson, Jr. | C10L 1/06 585/314 |
| 6,566,569 B1 | 5/2003 | Chen et al. | |
| 7,285,698 B2 | 10/2007 | Liu et al. | |
| 7,919,664 B2 | 4/2011 | Hommeltoft et al. | |
| 8,237,004 B2 | 8/2012 | Timken et al. | |
| 9,302,199 B2 | 4/2016 | Timken et al. | |
| 9,388,093 B2 | 7/2016 | Luo et al. | |
| 2008/0202161 A1 * | 8/2008 | Vazquez-Esparragoza | C10L 3/10 62/620 |
| 2011/0226669 A1 * | 9/2011 | Timken | B01J 31/0277 208/134 |
| 2011/0319694 A1 * | 12/2011 | Timken | C07C 2/60 585/719 |
| 2012/0051953 A1 | 3/2012 | O'Rear | |
| 2014/0039231 A1 * | 2/2014 | Timken | B01D 3/009 585/251 |
| 2015/0141728 A1 * | 5/2015 | Laricchia | C07C 7/005 585/802 |
| 2016/0001255 A1 | 1/2016 | Luo et al. | |
| 2016/0002542 A1 | 1/2016 | Lacheen | |
| 2016/0168053 A1 | 6/2016 | Kalnes et al. | |
| 2016/0168054 A1 | 6/2016 | Kalnes et al. | |
| 2016/0237004 A1 | 8/2016 | Wang et al. | |
| 2016/0264494 A1 | 9/2016 | Mohr et al. | |

OTHER PUBLICATIONS

The Role of Natural Gas Liquids (NGL's) in the American Petrochemical Boom; Kinder Morgan White Paper.

PCT International Search Report, International Patent Appl. No. PCT/IB2018/054078, dated Aug. 21, 2018.

* cited by examiner

Natural Gas Liquid (C₃ – C₆) Upgrading to Alkylate Gasoline, Jet or Diesel

Natural Gas Liquid (C$_5$ – C$_6$) Upgrading to Alkylate Jet or Diesel n-Butane or Isobutane Upgrading to Alkylate Gasoline n-Pentane or Isopentane Upgrading to Alkylate Jet and Diesel

NATURAL GAS LIQUID UPGRADING BY IONIC LIQUID CATALYZED ALKYLATION

TECHNICAL FIELD

This application is directed to processes and integrated process units for making alkylate products from natural gas liquids.

BACKGROUND

With the recent, unprecedented success of the hydraulic fracturing and horizontal drilling in shale and tight rock formations, the natural gas production has increased exponentially. Raw natural gas typically consists primarily of methane. It also contains varying amounts of heavier hydrocarbons such as ethane, propane, butanes, pentanes and even higher molecular weight hydrocarbons. All these heavier hydrocarbons in raw natural gas are collectively referred to as natural gas liquid.

The rapid growth in hydraulic fracturing has resulted in a surge in production of natural gas liquid. Availability of low cost ethane and propane has allowed new petrochemical investments in ethylene crackers and propane dehydrogenation plants in the US and elsewhere for polymer and chemicals production. The increased surplus volumes of propane, butanes, pentanes and hexanes, however, has exceeded the demand of these materials in industry, and thus created a need for a new hydrocarbon conversion process to convert these low value materials into higher value products.

Dehydrogenation processes to convert propane to propylene and isobutane to isobutylene (2-methylpropene) have been practiced before. Several commercial processes, such as Catofin® Dehydrogenation offered by CBI, Oleflex™ Technology by UOP and STAR process® by ThyssenKrupp Industrial Solutions, are practiced in the industry, and high purity olefin products (99%+purity) are produced for polymer or petrochemical applications. Dehydrogenating is limited by thermodynamic equilibrium, and the conversion per pass is typically less than 50%. The boiling point difference between the paraffin and olefin molecules after the dehydrogenating is very small and their separation is very difficult. In order to obtain the high purity olefin from the dehydrogenation reaction product mixture, the conventional dehydrogenation processes use a multi-stage paraffin/olefin splitter (e.g., multiple distillation columns). These olefin/paraffin separations are very energy intensive and costly.

Improved processes and equipment are needed for upgrading of natural gas liquid into valuable alkylate products.

SUMMARY

This application provides a process for making one or more alkylate products, comprising:

a. dehydrogenating a natural gas feedstock comprising saturated hydrocarbons in a dehydrogenation reactor to produce a mixture comprising one or more olefins and one or more unconverted paraffins;

b. without further purification or modification, sending the mixture to a single alkylation reactor that is not thermally coupled with the dehydrogenation reactor; and c. alkylating the one or more olefins with an isoparaffin in the single alkylation reactor, using an ionic liquid catalyst, to produce the one or more alkylate products.

This application also provides an integrated process unit for making one or more alkylate products, comprising:

a. a dehydrogenation reactor that converts paraffins in a natural gas feedstock to produce a mixture comprising one or more olefins and one or more unconverted paraffins;

b. a single alkylation reactor, comprising an ionic liquid catalyst, that is fluidly connected to the dehydrogenation reactor, that receives the mixture and converts the one or more olefins into the one or more alkylate products;

c. a separator, fluidly connected to and following the single alkylation reactor, that separates an effluent from the single alkylation reactor into a catalyst phase and a hydrocarbon phase;

d. a distillation unit, fluidly connected to and following the separator, that receives the hydrocarbon phase and separates the hydrocarbon phase into the one or more alkylate products, an unreacted paraffin phase, and an isoparaffin phase;

e. a first recycle line from the distillation unit that feeds the unreacted paraffin phase to the dehydrogenation reactor; and f. a second recycle line from the distillation unit that feeds the isoparaffin phase to the single alkylation reactor.

The present invention may suitably comprise, consist of, or consist essentially of, the elements in the claims, as described herein.

GLOSSARY

Figure 1:
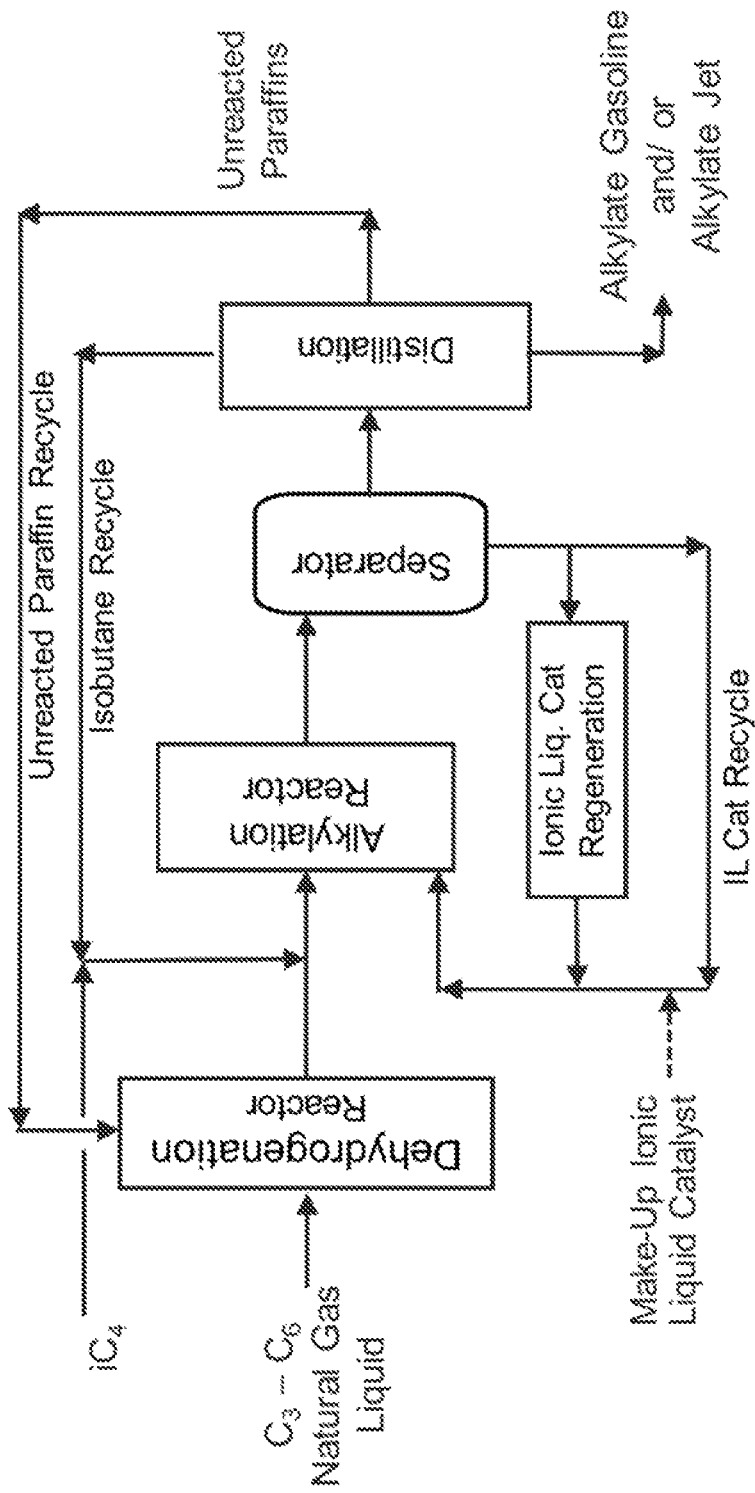
FIG. 1 is a schematic diagram of an exemplary integrated process unit for making one or more alkylate products by a natural gas liquid ($C_3$-$C_6$) conversion process that produces alkylate gasoline, alkylate jet fuel and/or alkylate diesel fuel.

A "natural gas" is a gas that is comprised primarily of methane, and which when properly processed can be used as fuel by residential, commercial, or industrial consumers. The vast majority of natural gas, typically 70-90 percent, is methane. The remaining approximately 10-30 percent is various natural gas liquids.

A "natural gas liquid" is a hydrocarbon in natural gas that condenses at atmospheric pressure to become liquid. Natural gas that contains a lot of natural gas liquids and condensates is referred to as wet gas, while gas that is primarily methane, with little to no liquids in it when extracted, is referred to as dry gas.

"Hydraulic fracturing" refers to the forcing open of fissures in subterranean rocks by introducing liquid at high pressure, especially to extract oil or gas.

"Dehydrogenation" is a chemical reaction that involves the removal of hydrogen from an organic molecule. It is the reverse of hydrogenation. Dehydrogenation is an important reaction because it converts alkanes, which are relatively inert and thus low-valued, to olefins, which are reactive and thus more valuable.

"Alkylation" is the transfer of an alkyl group from one molecule to another. The process combines an unsaturated light hydrocarbon (olefin) with an isoparaffin to produce one or more alkylate products.

"Isomerization" refers to the process by which one molecule is transformed into another molecule which has exactly the same number of atoms, but the atoms have a different arrangement e.g. A-B-C→ B-A-C (these related molecules are known as isomers).

"Paraffin" refers to a fully saturated hydrocarbon, also known as an alkane. Paraffins include both straight-chain and branched alkanes.

"Isoparaffin" refers to any branched-chain isomer of a straight-chain alkane.

"Normal paraffin" refers to a straight-chain alkane.

"Gasoline" is a liquid hydrocarbon used as a fuel in internal combustion engines. Gasoline has a carbon number of predominately four to twelve.

"Naphtha" is a lighter hydrocarbon product having a naphtha boiling range from 90° F. to 300° F. (32° C. to 149° C.).

A "gasoline blending component" may be either a gasoline or a naphtha suitable for blending into a gasoline.

"Boiling range" is the 10% boiling point to the final boiling point (99.5%), inclusive of the end points, as measured by ASTM D2887-16a or ASTM D86-16a.

"Gasoline boiling range' refers to hydrocarbons having a boiling range from 100° F. to 400° F. (38° C. to 204° C.).

"Middle distillate" is a hydrocarbon product having a middle distillate boiling range from 250° F. to 700° F. (121° C. to 371° C.). The term "middle distillate" includes the diesel fuel, heating oil, jet fuel, and kerosene boiling range fractions. It may also include a portion of naphtha or light oil.

A "middle distillate blending component" may be one or more of a diesel fuel, a heating oil, a jet fuel, or a kerosene that is suitable for blending into one of these products.

"Light oil" is a heavier hydrocarbon product having a light oil boiling range that starts near 600° F. (316° C.) or higher. The term "light oil boiling range" refers to hydrocarbons having a boiling range from 600° F. to 1100° F. (316° C. to 593° C.).

"Jet fuel" is a type of aviation fuel designed for use in aircraft powered by gas-turbine engines. Jet fuel is a hydrocarbon product having a jet fuel boiling range. The term "jet fuel boiling range" refers to hydrocarbons having a boiling range from 250° F. to 550° F. (121° C. to 288° C.).

"Diesel fuel" is any liquid fuel used in diesel engines, whose fuel ignition takes place, without any spark, as a result of compression of the inlet air mixture and then injection of fuel. The term "diesel fuel boiling range" refers to hydrocarbons having a boiling range from 250° F. to 700° F. (121° C. to 371° C.).

"Predominant", in the context of this disclosure, means 80 to 100 wt %.

DETAILED DESCRIPTION

The natural gas feedstock comprises mostly straight-chain hydrocarbons and some branched hydrocarbons. The hydrocarbons can comprise any combination of C2 to C6 paraffins. In one embodiment, the natural gas feedstock comprises from C2 to C6 normal paraffins and isoparaffins. In one embodiment, the natural gas feedstock is one of a C2, a C3, a C4, a C5, or a C6 paraffin. In one embodiment, the natural gas feedstock is produced by a hydraulic fracturing.

The natural gas feedstock, or fraction thereof, is dehydrogenated in a dehydrogenation reactor to produce a mixture comprising one or more olefins and one or more unconverted (or unreacted) paraffins. The dehydrogenation is purposefully not complete, such that the mixture comprises greater than 20 wt % of the one or more unconverted paraffins, such as from 21 to 90 wt %, or from 30 to 80 wt % of the one or more unconverted paraffins.

The dehydrogenation reaction can be highly exothermic and may require an elevated temperature. In one embodiment, the dehydrogenating conditions include an elevated temperature greater than 375° C., such from 400° C. to 900 ° C., or from 475° C. to 825° C. In one embodiment, the dehydrogenating conditions are adjusted depending on the one or more unconverted paraffins, that were originally present in the natural gas feedstock, to provide an optimum conversion. In one embodiment, the elevated temperature is adjusted depending on the carbon number and chemical structures of the hydrocarbons in the natural gas feedstock. For example, isobutane is easier to dehydrogenate than n-butane. High carbon number paraffins (i.e., C4-C6 paraffins) dehydrogenate at lower elevated temperatures, but they are more susceptible to coking and undesirable side reactions.

In one embodiment, the dehydrogenating conditions include a low pressure, such as less than 200 psig (1379 kPa) or less than 150 psig (1034 kPa), further such as from 0 to 100 psig (0 to 689 kPa), or at around 1 atm (14.7 psig or 101 kPa). In one embodiment, the dehydrogenating conditions include a pressure from 0 to 100 psig (0 to 689 kPa), and a temperature from 400° C. to 900° C. The process does not need a multi-stage paraffin/olefin splitter or other equipment to purify the mixture before it is alkylated. Instead, our process comprises sending the mixture to a single alkylation reactor without further purification or modification. The mixture is sent to the single alkylation reactor, and the alkylation reactor is not thermally coupled with the dehydrogenation reactor. By not thermally coupled is meant that the dehydrogenation reactor and the single alkylation reactor are separate and they are not coupled by means of heat pipes or other thermal couplings, e.g., they are not a shell and tube type reactor arrangement.

In one embodiment, the alkylation reactor is fluidly connected to the dehydrogenation reactor such that the effluent from the dehydrogenation reactor passes directly to the alkylation reactor. In one embodiment, no equipment is included in a fluid connection between the dehydrogenation reactor and the single alkylation reactor to provide a separation of the one or more olefins and the one or more unconverted paraffins in the mixture.

The alkylating of the one or more olefins in the mixture is done with an isoparaffin. The isoparaffin can be any C4 to C10 isoparaffin. In one embodiment, the isoparaffin is an isobutane, an isopentane, an isohexane or a combination thereof.

In one embodiment, a molar ratio of the isoparaffin to the one or more olefins in the single alkylation reactor is greater than 1:1, such as from 4:1 to 12:1.

The alkylating conditions are selected to provide the desired alkylate product yields and quality. The alkylation reaction is generally carried out in a liquid hydrocarbon phase, in a single batch alkylation reactor, a single semi-batch alkylation reactor, or a continuous alkylation reactor. Examples of a continuous alkylation reactor is a nozzle loop alkylation reactor or a continuously stirred tank reactor (CSTR). Catalyst volume in the alkylation reactor is in the range of 1 vol % to 80 vol %, for example from 2 vol % to 70 vol %, from 3 vol % to 50 vol %, or from 5 vol % to 25 vol %. In some embodiments, vigorous mixing can be used to provide good contact between the reactants and the catalyst. The alkylation reaction temperature can be in the range from −40° C. to 150° C., such as −20° C. to 100° C., or −15° C. to 50° C. The pressure can be in the range from atmospheric pressure to 8000 kPa. In one embodiment the pressure is kept sufficient to keep the reactants in the liquid phase. The residence time of reactants in the reactor can be in the range of a second to 360 hours. Examples of residence times that can be used include 0.5 min to 120 min, 1 min to 120 min, 1 min to 60 min, and 2 min to 30 min.

In one embodiment, the one or more alkylate products that are produced by the process or the integrated process unit is one or more of an alkylate gasoline, and alkylate middle distillate, or an alkylate light oil. In one embodiment, the one or more alkylate products that are produced by the process or the integrated process unit are selected from the group consisting of an alkylate gasoline, an alkylate jet fuel, an alkylate diesel fuel, and mixtures thereof. In different embodiments, we disclose an integrated upgrading process and an integrated process unit that converts a natural gas liquid into alkylate gasoline, alkylate jet fuel, and alkylate diesel fuel.

With the large and increasing volumes of new, low-cost natural gas liquid feedstocks that are readily available, our upgrading process can be desirable and cost effective. In some embodiments, the synthetic fuels created by these processes and integrated process units described herein are high quality fuel blending components with excellent fuel properties (Octane Numbers, cold flow properties, Cetane Index, etc.). In one embodiment, our alkylate products are predominantly comprised of isoparaffins, with little or no aromatics and olefins. The impurity contents (e.g., sulfur, nitrogen, chloride, and/or oxygenates) are also very low. These high-quality, clean-burning alkylate products can be blended to the typical fuels produced by oil refineries to meet the environmental regulations for clean fuels.

In one embodiment, the one or more alkylate products comprise less than 10 wppm chloride, such as from zero to 5 wppm chloride.

In one embodiment, an alkylate middle distillate is produced. In some embodiments, the alkylate middle distillate can be fully saturated, such as having a Bromine number less than 1. In one embodiment, the alkylate product is made of mostly paraffinic hydrocarbons with negligible amounts of aromatics and olefins. In one embodiment, the alkylate middle distillate can comprise less than 10 wppm chloride. The alkylate product shows excellent properties for use in gasoline, jet or diesel.

FIG. 1 shows one embodiment for upgrading of natural gas liquid to alkylate gasoline and/or alkylate jet fuel using dehydrogenation and alkylation processes. In this figure the natural gas feedstock is a natural gas liquid that comprises C3-C6 paraffins, the isoparaffin is isobutane, and alkylate gasoline and/or alkylate jet fuel are produced. A fraction of natural gas liquid (a fraction containing $C_3$ or $C_4$ or $C_5$ or $C_6$) is dehydrogenated using a dehydrogenation catalyst to produce a mixture of olefins and unconverted paraffins. The olefin/paraffin mixture is then alkylated with isobutane in the alkylation reactor using an ionic liquid catalyst to produce alkylate products that boil in gasoline, jet, and diesel fuel boiling ranges. The effluent from the alkylation reactor is separated in a separator into a hydrocarbon phase, that is sent to a distillation unit, and into an ionic liquid phase that is regenerated (in part or in full) and/or recycled to the alkylation reactor. Isobutane is separated from the distillation unit and recycled to the alkylation reactor. An unconverted paraffin stream is also separated from the distillation section and recycled to the dehydrogenation reactor.

The overall process chemistry shown in FIG. 1 can be described as:

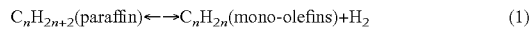

$$C_nH_{2n+2}(\text{paraffin}) \leftarrow \rightarrow C_nH_{2n}(\text{mono-olefins}) + H_2 \quad (1)$$

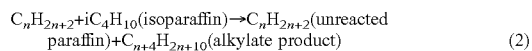

$$C_nH_{2n+2} + iC_4H_{10}(\text{isoparaffin}) \rightarrow C_nH_{2n+2}(\text{unreacted paraffin}) + C_{n+4}H_{2n+10}(\text{alkylate product}) \quad (2)$$

In one embodiment, as shown in Equation (1), natural gas liquid is first dehydrogenated to olefins using a dehydrogenation catalyst. In one embodiment, the dehydrogenation catalyst comprises a noble or non-noble metal such as Pt, Pd, Ni, Co, Fe, Sn, Rh, Ir, Ru, Re, W, Mo, or In, either as a single component or binary or ternary component in the form of alloys or solid solutions. The dehydrogenation catalyst can be a Pt-based catalyst (e.g., Pt or Pt—Sn on alumina or other support) or a non-noble metal such as nickel, molybdenum, cobalt, and tungsten, e.g., in combinations such as Ni/W, Ni/Mo, Co/Mo. In one embodiment, the dehydrogenation catalyst is a Pt-based catalyst, e.g. Pt, Pt—Sn, Pt—Re, Pt—In on a support such as alumina, silica, zirconia, titania, ceria, lanthanum oxide, magnesium oxide, either alone or in mixtures thereof. Examples of dehydrogenation catalysts that could be used for the dehydrogenating include $Pt/Al_2O_3$ catalyst, $Cr/Al_2O_3$ catalyst, Pt/carbon catalyst and a combination thereof. In one embodiment, the dehydrogenating is performed with a dehydrogenation catalyst comprising a $Pt/Al_2O_3$, a $Cr/Al_2O_3$, a Pt/carbon catalyst or a combination thereof. The dehydrogenation can be performed at an elevated temperature. Two references that teach suitable dehydrogenation processes include: Bert M. Weckhuysen & Robert A. Schoonheydt, "Alkane Dehydrogenation Over Supported Chromium Oxide Catalysts", Catalysis Today, 51, 1999, pp 223-232; and M. M. Bhasin, J. H. McCain, B. V. Bora, T. Imai, P. R. Pujado, "Dehydrogenation and Oxydehydrogenation of Paraffins to Olefins", Applied Catalysis A: General, 221, 2001, pp 397-419.

Again referring to FIG. 1, the mixture containing paraffins and olefins from the dehydrogenation reactor is sent to the alkylation reactor that uses an ionic liquid catalyst and isobutane (Equation 2). The ionic liquid catalyst is particularly effective in alkylating the mixture of paraffinic and olefinic hydrocarbons where olefins are selectively alkylated with isobutane. Fresh and recycled isobutane streams are added to the olefin feed mixture to make the isobutane/olefin molar ratio in the range of 4:1 to 12:1. Nearly 100% of the olefins are converted during the alkylating, and this leaves only the unconverted paraffins and isobutane. The unconverted feed paraffins and the alkylate product after the alkylating have a four (4) carbon number difference in their chemical formulas, and these molecules can be easily separated by simple distillation. In this embodiment, unconverted feed paraffins are recycled back effectively to the dehydrogenation reactor and isobutane is recycled back to the alkylation reactor.

Figure 2:
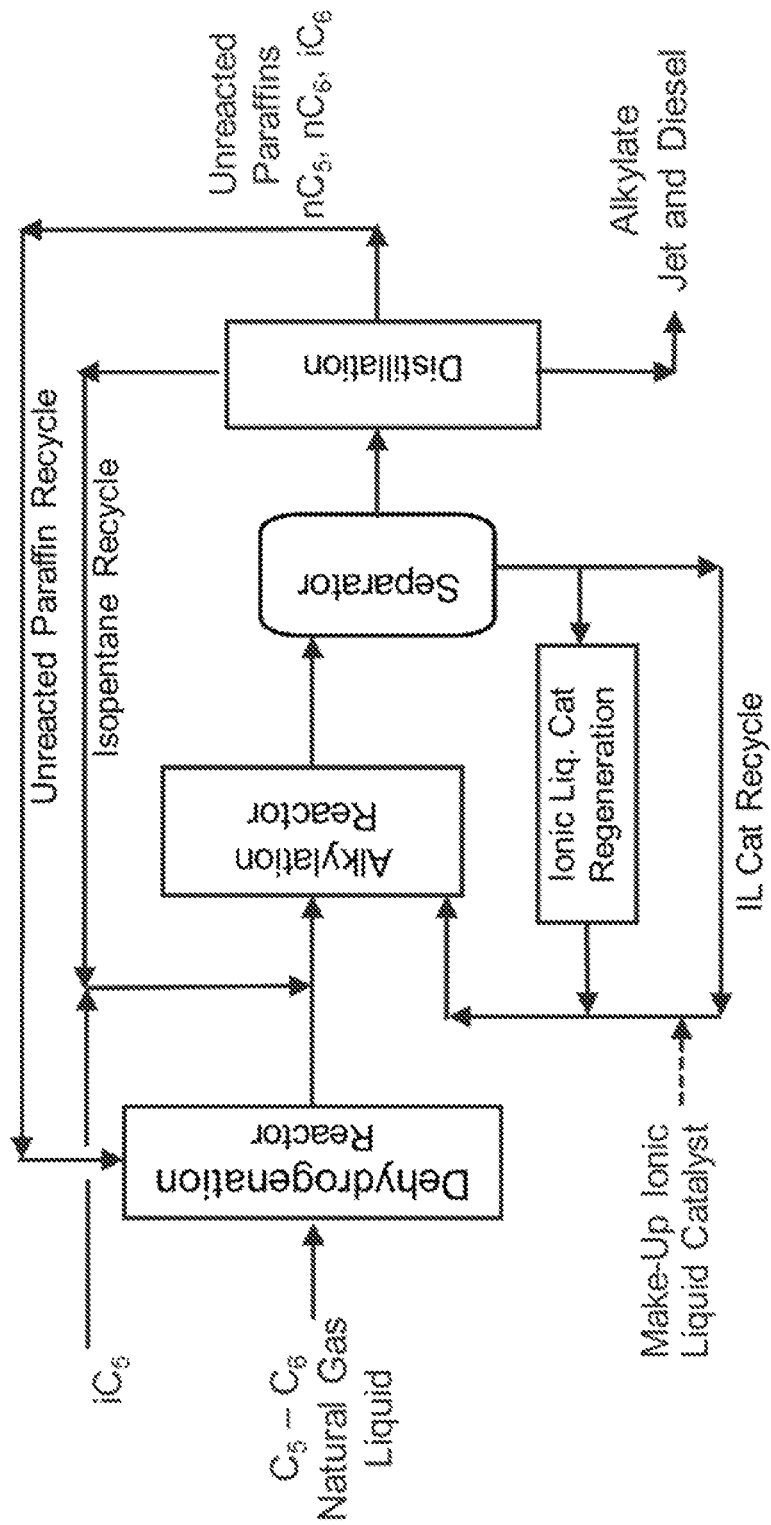
FIG. 2 is a schematic diagram of an exemplary integrated process unit for making one or more alkylate products by a natural gas liquid ($C_5$-$C_6$) conversion process that produces alkylate jet fuel and/or alkylate diesel fuel.

FIG. 2 shows another embodiment for upgrading of natural gas liquid to alkylate gasoline, alkylate jet fuel, or alkylate diesel fuel using dehydrogenation and alkylation. In this figure the natural gas feedstock is a natural gas liquid that comprises C5-C6 paraffins, the isoparaffin is isopentane, and alkylate jet fuel and/or alkylate diesel fuel are produced.

The overall process chemistry shown in FIG. 2 can be described as:

$$C_nH_{2n+2}(\text{paraffin}) \longleftrightarrow C_nH_{2n}(\text{mono-olefins}) + H_2 \quad (3)$$

$$C_nH_{2n+2} + C_nH_{2n} + iC_5H_{12}(\text{isoparaffin}) \rightarrow C_nH_{2n+2}(\text{unreacted paraffin}) + C_{n+5}H_{2n+12}(\text{alkylate product}) \quad (4)$$

Figure 3:
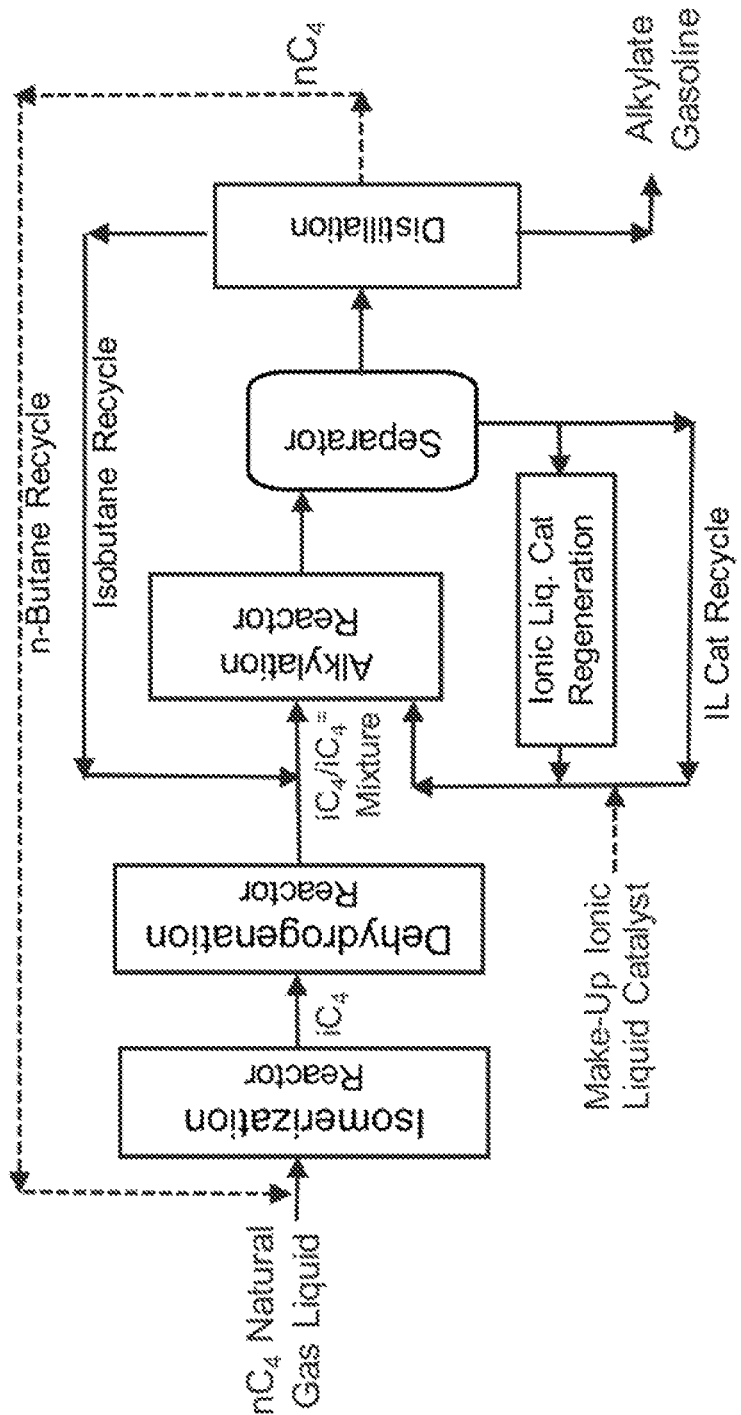
FIG. 3 is a schematic diagram of an exemplary integrated process unit for making alkylate gasoline by a natural gas liquid ($nC_4$ or $iC_4$) conversion process that produces alkylate gasoline.

FIG. 3 is a schematic diagram of another embodiment for upgrading of natural gas liquid to make alkylate gasoline. In this figure, the natural gas feedstock is a natural gas liquid comprising n-butane (or isobutane) and the isoparaffin is isobutane.

The overall process chemistry shown in FIG. 3 can be described as:

$$n\text{-}C_4H_{10}(n\text{-butane}) \rightarrow i\text{-}C_4H_{10}(\text{isobutane}) \quad (5)$$

$$i\text{-}C_4H_{10}(\text{isobutane}) \longleftrightarrow i\text{-}C_4H_8(\text{isobutylene}) + H_2 \quad (6)$$

$$i\text{-}C_4H_{10} + i\text{-}C_4H_8 \rightarrow C_8H_{18}(\text{alkylate}) \quad (7)$$

In FIG. 3, the n-butane is first isomerized to isobutane using an isomerization catalyst in an isomerization reactor (Equation 5). The isomerized reactor effluent is distilled to achieve an isobutane stream with over 90% isobutane purity. If an isobutane feed is available from another source of natural gas liquid, then the isomerization step in Equation 5 could be eliminated in this embodiment. The isobutane stream is then sent to the dehydrogenation reactor to convert the isobutane to isobutylene (Equation 6). The dehydrogenating can be controlled to only partially dehydrogenate the isoparaffin, such as to hydrogenate from 30 wt % to 60 wt % of the isoparaffin. For example, the dehydrogenating can be controlled to convert roughly about 50 wt % of the isobutane to isobutylene.

The dehydrogenation reactor effluent can be cooled down and compressed to separate hydrogen from the dehydrogenated isobutane and isobutylene mixture. The dehydrogenated isobutane and isobutylene mixture is liquefied by the cooling and can be sent to the alkylation reactor to produce an alkylate gasoline. In this embodiment, the alkylate gasoline contains a predominant amount of $C_8$ alkylate. This process configuration shown in FIG. 3 carries only a limited amount of unconverted n-butane from the isomerization reactor to the dehydrogenation reactor and then to the alkylation reactor. The carried over n-butane (shown as n-Butane Recycle) can be recovered easily, from the distillation column that is located after the alkylation reactor, and sent back to the isomerization reactor.

Figure 4:
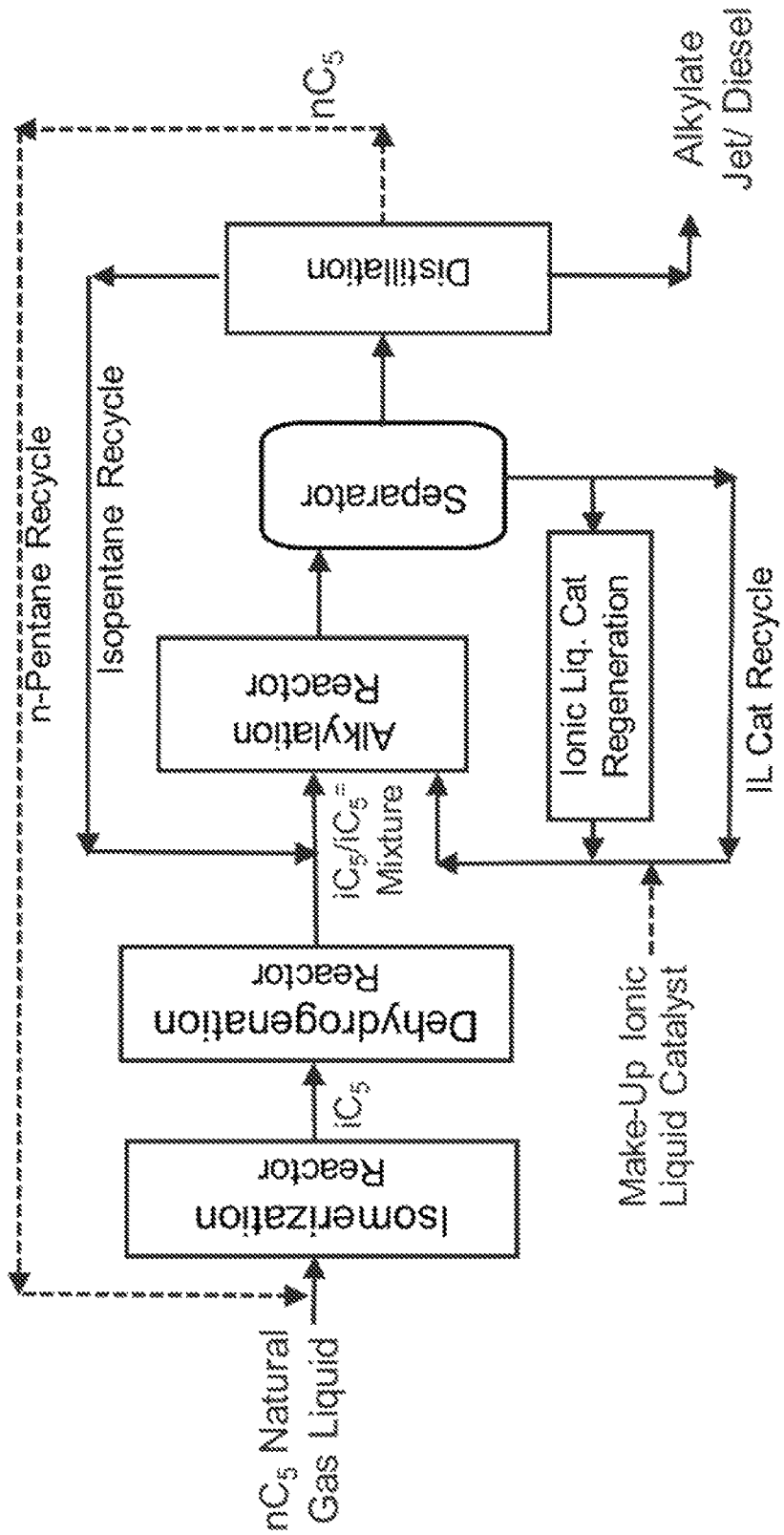
FIG. 4 is a schematic diagram of an exemplary integrated process unit for making alkylate jet fuel and/or alkylate diesel fuel by a natural gas liquid ($nC_5$ or $iC_5$) conversion process that produces alkylate jet fuel and/or alkylate diesel fuel.

In one embodiment, the process additionally comprises isomerizing the natural gas feedstock prior to the dehydrogenating. This feature is shown in FIG. 3 and FIG. 4. The isomerizing will convert some of the straight-chain hydrocarbons to produce the isoparaffin that is subsequently alkylated in the alkylation reactor. In one embodiment, the process comprises isomerizing an n-butane to produce an isobutane, and the isobutane is the isoparaffin. In one embodiment, the integrated process unit additionally comprises an isomerization reactor connected to and placed before the dehydrogenation reactor, wherein the isomerization reactor isomerizes the natural gas feedstock to make at least a portion of an isoparaffin that is fed to the alkylation reactor.

Any processes that are known for performing n-butane isomerization to isobutane can be used in the configuration shown in FIG. 3. In one embodiment, the isomerization is done in a fixed bed reactor using an isomerization catalyst, such as for example, a Pt/Alumina catalyst with a chloride promoter. One reference that describes processes for n-butane isomerization to isobutane is Robert A. Myers, "Handbook of Petroleum Refining Processes", Sec. 9.7, 3rd Ed., McGraw-Hill, New York, N.Y. (2003).

In some embodiments, such as when using a high activity isomerization catalyst, the isomerizing is performed under moderate conditions, including one or more of: an isomerization temperature from ~180-220° C., an isomerization pressure of 1.5-3 MPa, and a linear hourly space velocity (LHSV) of about 2 h$^{-1}$.

In one embodiment, a small amount of $H_2$ can be fed to the isomerization reactor to minimize coking of the isomerization catalyst. This process feature is described in S. Raseev, "Thermal and Catalytic Processes in Petroleum Refining", Marcel Dekker, New York, N.Y. (2003).

In one embodiment, the dehydrogenating is controlled to minimize the formation of coke while also controlling the amount of conversion of the n-butane to isobutane. For example, the dehydrogenation reactor temperature and the number of the dehydrogenation reactor beds can be optimized to produce roughly a 50:50 molar mixture of isobutane to isobutylene. By controlling the dehydrogenation conversion to about 50% of isobutane to isobutylene, the whole process is nearly stoichiometrically balanced and the amounts of recycle streams can be minimized.

The final alkylation product produced by the process shown in FIG. 3 can be an alkylate gasoline that makes an excellent gasoline blending component. In one embodiment, the alkylate product is made of mostly paraffinic hydrocarbons with negligible amounts of aromatics and olefins. The sulfur level can be about 10 ppm or less. The alkylate product shows excellent properties that contribute to the quality of a gasoline, such as: high Octane Number, low impurities, and good boiling range.

FIG. 4 is a schematic diagram of another embodiment for upgrading of natural gas liquid to make alkylate products. In this figure, the natural gas feedstock is a natural gas liquid comprising n-pentane and the isoparaffin is isopentane. Here, the process concept is similar to that shown in FIG. 3, but the process uses n-pentane or isopentane as the starting material, and a mixture of isopentane and isopentenes (2-methyl-1-butene, 2-methyl-2-butene, 3-methyl-2-butene, and 2,2-dimethylpropene) is created after the dehydrogenation step. The mixture of isopentane and isopentenes is alkylated to produce the final alkylate product that can be predominately $C_{10}$ alkylate.

The overall process chemistry shown in FIG. 4 can be described as:

$$n\text{-}C_5H_{12}(n\text{-pentane}) \rightarrow i\text{-}C_5H_{12}(\text{isopentane}) \quad (8)$$

$$i\text{-}C_5H_{12}(\text{isopentane}) \longleftrightarrow i\text{-}C_5H_{10}(\text{isopentene}) + H_2 \quad (9)$$

$$i\text{-}C_5H_{12} + i\text{-}C_5H_{10} \rightarrow C_{10}H_{22}(\text{alkylate product}) \quad (10)$$

In some embodiments, the final alkylate product produced by the process of FIG. 4 can be used as-is for gasoline.

Another process option is to further distill the alkylate product to split the alkylate product into a light and a heavy fraction, such as a light gasoline fraction (such as a naphtha), and a middle distillate fraction. The distillation can, for example, include cutting at 250° F. (121° C.) or at another cut temperature depending on the alkylate product blending needs. In one embodiment, the bottoms distillation fraction from a distillation column used in the process can be used as a jet fuel and/or a diesel fuel. In one embodiment, for example, wherein the one or more olefins is at least 60 wt % isopentene, the isoparaffin is an isopentane, and the one or more alkylate products comprises an alkylate middle distillate with a smoke point of 35 or higher, a freeze point of −40° C. or lower, a bromine number less than 2, and 10 wppm or less of a sulfur.

As shown in the figures, the process can additionally comprise the steps of distilling an effluent from the single alkylation reactor into separate fractions comprising: the one or more alkylate products, an unreacted isoparaffin fraction, and an unreacted paraffin fraction. Recycling of the unreacted isoparaffin fraction to the single alkylation reactor, and recycling the unreacted paraffin fraction to the dehydrogenation reactor can also be used.

In one embodiment, the process additionally comprises maintaining an overall alkylation activity of the ionic liquid catalyst by separating a used ionic liquid catalyst from an effluent of the single alkylation reactor, regenerating a portion of the used ionic liquid catalyst, and returning both a regenerated ionic liquid catalyst and the used ionic liquid catalyst to the single alkylation reactor.

Various configurations of the integrated process unit are shown in FIGS. 1-4. In one embodiment, the integrated process unit additionally comprises a connection between the separator and the single alkylation reactor, wherein the connection passes a portion of a used ionic liquid through a regeneration unit and transports a blended stream comprising the used ionic liquid and a regenerated ionic liquid from the regeneration unit to the single alkylation reactor to maintain an activity of the ionic liquid catalyst for an alkylation. In one embodiment, the integrated process unit additionally comprises an inlet, on the connection, that feeds a co-catalyst comprising a chloride to the mixture of the used ionic liquid and the regenerated ionic liquid. In one embodiment, the integrated process unit additionally comprises a second inlet, on the connection, that feeds a make-up ionic liquid catalyst to the mixture of the used ionic liquid and the regenerated ionic liquid.

In one embodiment, the integrated process unit additionally comprises a third inlet, in a line between the dehydrogenation reactor and the single alkylation reactor, that feeds either a recycled isoparaffin stream from the second recycle line or a combination of a fresh isoparaffin stream and a recycled isoparaffin stream from the second recycle line. In some embodiments, no fresh isoparaffin stream is needed to be fed to the alkylation reactor. These embodiments are shown in FIGS. 3 and 4.

Depending on the natural gas feedstock source and the alkylating conditions used in the process shown in FIG. 4, the one or more alkylate products can be an alkylate gasoline, an alkylate jet fuel, an alkylate diesel fuel, and mixtures thereof. In one embodiment, the alkylate product is mostly a paraffinic hydrocarbon with negligible amounts of aromatics and olefins. In one embodiment, the sulfur level in the alkylate product is about 50 wppm or less, such as from zero to 10 wppm sulfur. In one embodiment the sulfur level in the alkylate product can be about 1 wppm or less. In one embodiment, the alkylate product shows excellent properties for gasoline, jet fuel, or diesel fuel.

In one embodiment, the process produces an alkylate gasoline with a high octane number. Examples of high octane numbers are 82 or higher, greater than 85, greater than 90, and greater than 95. In one embodiment the alkylate gasoline has a RON from 90 to 105. Different methods are used for calculating octane numbers of fuels or fuel blend components. The Research-method octane number (RON) is determined using ASTM D 2699-07a. RON employs the standard Cooperative Fuel Research (CFR) knock-test engine. Additionally, the Research-method octane number may be calculated [RON (GC)] from gas chromatography boiling range distribution data. The RON (GC) calculation is described in the publication, Anderson, P. C., Sharkey, J. M., and Walsh, R. P., "Journal Institute of Petroleum", 58 (560), 83 (1972).

Alkylation processes for making alkylate gasoline with low volatility and high octane number are described in U.S. Pat. No. 7,432,408 and U.S. patent application Ser. No. 12/184,109, filed on Jul. 31, 2008.

In one embodiment, wherein the one or more olefins comprise a 2-butene and the isoparaffin is an isobutane, the one or more alkylate products is an alkylate gasoline with a high RON, such as having a RON of 85 or higher, or from 90 to 105. In one embodiment, wherein the one or more olefins is at least 70 wt % isobutylene, the isoparaffin is an isobutane, and the one or more alkylate products comprises an alkylate gasoline with a RON of 94 or higher, a RVP of 3.5 psi or less, and 5 wppm or less of a sulfur. In one embodiment, wherein the one or more olefins is at least 90 wt % isobutylene and the isoparaffin is an isobutane, the one or more alkylate products can comprise an alkylate gasoline with a high RON (90 to 105, or 94 or higher) and with a low RVP (less than 5 psi, or 3.5 psi or less).

Ionic Liquid Catalyst:

The ionic liquid catalyst is composed of at least two components which form a complex. To be effective at alkylation the ionic liquid catalyst is acidic. The acidic ionic liquid catalyst comprises a first component and a second component. The first component of the catalyst will typically comprise a Lewis Acidic compound selected from components such as Lewis Acidic compounds of Group 13 metals, including aluminum halides, alkyl aluminum halide, gallium halide, and alkyl gallium halide (see International Union of Pure and Applied Chemistry (IUPAC), version3, October 2005, for Group 13 metals of the periodic table). Other Lewis Acidic compounds besides those of Group 13 metals may also be used. In one embodiment the first component is aluminum halide or gallium halide or iron halide or alkyl aluminum halide. For example, aluminum trichloride may be used as the first component for preparing the ionic liquid catalyst.

The second component making up the ionic liquid catalyst is an organic salt or mixture of salts. These salts may be characterized by the general formula $Q^+A^-$, wherein $Q^+$ is an ammonium, phosphonium, boronium, iodonium, or sulfonium cation and $A^-$ is a negatively charged ion such as $Cl^-$, $Br^-$, $ClO_4^-$, $NO_3^-$, $BF_4^-$, $BCl_4^-$, $PF_6^-$, $SbF_6^-$, $AlCl_4^-$, $ArF_6^-$, $TaF_6^-$, $CuCl_2^-$, $FeCl_3^-$, $SO_3Cl$, $SO_3C^-$, and 3-sulfurtrioxyphenyl. In one embodiment the second component is selected from those having quaternary ammonium halides containing one or more alkyl moieties having from about 1 to about 9 carbon atoms, such as, for example, trimethylamine hydrochloride, methyltributylammonium, 1-butylpyridinium, or hydrocarbyl substituted imidazolium halides, such as for example, 1-ethyl-3-methyl-imidazolium chloride. In one embodiment the ionic liquid catalyst is a chloroaluminate ionic liquid having the general formula RR' R" N H$^+$ Al$_2$Cl$_7^-$, or RR' R" P H$^{30}$ Al$_2$Cl$_7^-$, wherein RR' and R" are alkyl groups containing 1 to 12 carbons.

In one embodiment, the ionic liquid catalyst comprises an alkyl substituted pyridinium chloroaluminate or an alkyl substituted imidazolium chloroaluminate of the general formulas A and B, respectively.

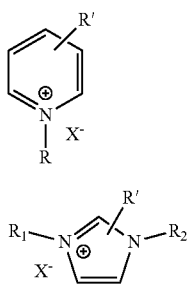

In the formulas A and B, R is H, methyl, ethyl, propyl, butyl, pentyl or hexyl group, R'=H, methyl, ethyl, propyl, butyl, pentyl or hexyl group, X is a chloroaluminate, and $R_1$ and $R_2$ are H, methyl, ethyl, propyl, butyl, pentyl or hexyl group. The ionic liquid catalyst may also comprise a derivative of either of the structures A or B in which one or more of the hydrogens attached directly to carbon in the ring has been replaced by an alkyl group. In the formulas A and B: R, R', $R_1$ and $R_2$ may or may not be the same. Alternatively the ionic liquid catalyst is a chloroaluminate ionic liquid having the general formula RR' R" R'" $N^+$ $Al_2Cl_7^-$ or RR' R" R'" P $Al_2Cl_7^-$, wherein RR', R" and R'" are alkyl groups containing 1 to 12 carbons.

The presence of the first component should give the ionic liquid a Lewis or Franklin acidic character. Generally, the greater the mole ratio of the first component to the second component, the greater the acidity of the ionic liquid mixture.

Ionic Liquid Co-Catalyst:

In one embodiment, a co-catalyst is added to the ionic liquid catalyst to boost the overall acidity and change the selectivity of the ionic liquid catalyst. The co-catalyst can be a halide containing additive, such as a co-catalyst comprising a chloride. The halide containing additive can be selected, and added to the ionic liquid catalyst, to provide increased yield of an alkylate product. Examples of halide containing additives are hydrogen halide, metal halide, and combinations thereof. In one embodiment, the halide containing additive may be a Bronsted acid. Examples of Bronsted acids are hydrochloric acid (HCl), hydrobromic acid (HBr), and trifluoromethanesulfonic acid. The use of halide containing additives with ionic liquid catalysts is disclosed in U.S. Published Patent Application Nos. 2003/0060359 and 2004/0077914. In one embodiment the halide containing additive is a fluorinated alkane sulphonic acid having the general formula:

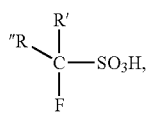

wherein R'=Cl, Br, I, H, an alkyl or perfluoro alkyl group, and R"=H, alkyl, aryl or a perfluoro alkoxy group.

Examples of metal halides that may be used are NaCl, LiCl, KCl, $BeCl_2$, $CaCl_2$, $BaCl_2$, $SrCL_2$, $MgCl_2$, $PbCl_2$, CuCl, $CuCl_2$, $ZrCl_4$ and AgCl, as described by Roebuck and Evering (Ind. Eng. Chem. Prod. Res. Develop., Vol. 9, 77, 1970). In one embodiment, the halide containing additive contains one or more IVB metal compounds, such as $ZrCl_4$, $ZrBr_4$, $TiCl_4$, $TiCl_3$, $TiBr_4$, $TiBr_3$, $HfCl_4$, or $HfBr_4$, as described by Hirschauer et al. in U.S. Pat. No. 6,028,024.

In one embodiment, the halide containing additive is added at a level that provides increased yield of an alkylate jet fuel or an alkylate diesel fuel. Adjusting the level of the halide containing additive level can change the selectivity of the alkylation reaction. For example, when the level of the halide containing additive, e.g., hydrochloric acid, is adjusted lower, the selectivity of the alkylation reaction shifts towards producing heavier products. The effects of increasing a molar ratio of olefin to HCl in the feed to an ionic liquid alkylation reactor (adjusting the level of the hydrochloric acid lower) on the yield of C10+ products in the alkylate produced is described in U.S. Pat. No. 7,919,664.

In one embodiment, a co-catalyst comprising a chloride is added to the ionic liquid catalyst. In one embodiment, the co-catalyst comprising a chloride that is added to the ionic liquid catalyst is an alkyl halide that generates anhydrous HCl in the alkylation reactor.

Test Method Descriptions:

API Gravity is measured by ASTM D 287-12b or ASTM D 1298-12b. Specific Gravity is measured by ASTM D1298-12b.

Average density is measured by ASTM D1298-12b or ASTM D4052-16. Average density is reported in g/ml, at the reference temperature of 15° C.

The test methods used for boiling range distributions of the compositions in this disclosure are ASTM D2887-16a and ASTM D86-16a. The test method by ASTM D2887-16a is referred to herein as "SIMDIST". Using SIMDIST, the boiling range distribution determination by distillation is simulated by the use of gas chromatography. The boiling range distributions obtained by this test method are essentially equivalent to those obtained by true boiling point (TBP) distillation (see ASTM Test Method D2892), but are not equivalent to results from low efficiency distillations such as those obtained with ASTM Test Methods D86 or D1160. ASTM D86-16a can be used for boiling range distributions of the alkylate products boiling in the naphtha boiling range or the gasoline boiling range.

Average molecular weight is calculated based on the composition determined by the gas chromatography analysis using the chemical formula and the wt % of each component.

Reid Vapor Pressure (RVP) is measured directly by ASTM D5191-15. Alternatively, Reid Vapor Pressure (RVP) is calculated based on the composition determined by the gas chromatography analysis using the vapor pressure and the mol % of each component. To convert Reid vapor pressure expressed in psi, multiply the result by 6.895 to obtain the Reid vapor pressure in kPa.

Total weight percents of carbon, hydrogen, and nitrogen (C/H/N) is determined with a Carlo Erba 1106 Analyzer by ASTM D5291-16. Low level nitrogen is separately determined by oxidative combustion and chemiluminescence by D4629-12. Sulfur is measured by ultraviolet fluorescence by ASTM 5453-16e1. Chloride is measured by x-ray fluorescence (XRF).

Flash Point is measured in a small scale closed-cup apparatus by D3828-16a. Smoke Point is measured by D1322-15e1. Cloud Point is measured by ASTM D5773-17. Freeze Point is measured by ASTM D5972-16. Aniline Point is measured by ASTM D611-12(Reapproved 2016). Bromine Number is measured by ASTM D1159-07(Reapproved 2012).

Different methods are used for calculating octane numbers of fuels or fuel blend components. The Motor-method octane number (MON) is determined using ASTMD 2700-

16a. The Research-method octane number (RON) is determined using ASTM D2699-16e1. MON and RON both employ the standard Cooperative Fuel Research (CFR) knock-test engine.

The Calculated Cetane Index is calculated according to ASTM D4737-10(Reapproved 2016).

6×6 Assay, herein refers to ASTM D5443-14, Standard Test Method for Paraffin, Naphthene, and Aromatic Hydrocarbon Type Analysis in Petroleum Distillates Through 200° C. by Multi-Dimensional Gas Chromatography, ASTM International, West Conshohocken, Pa., 2014.

The transitional term "comprising", which is synonymous with "including," "containing," or "characterized by," is inclusive or open-ended and does not exclude additional, un-recited elements or method steps. The transitional phrase "consisting of" excludes any element, step, or ingredient not specified in the claim. The transitional phrase "consisting essentially of" limits the scope of a claim to the specified materials or steps "and those that do not materially affect the basic and novel characteristic(s)" of the claimed invention.

For the purposes of this specification and appended claims, unless otherwise indicated, all numbers expressing quantities, percentages or proportions, and other numerical values used in the specification and claims, are to be understood as being modified in all instances by the term "about." Furthermore, all ranges disclosed herein are inclusive of the endpoints and are independently combinable. Whenever a numerical range with a lower limit and an upper limit are disclosed, any number falling within the range is also specifically disclosed. Unless otherwise specified, all percentages are in weight percent.

Any term, abbreviation or shorthand not defined is understood to have the ordinary meaning used by a person skilled in the art at the time the application is filed. The singular forms "a," "an," and "the," include plural references unless expressly and unequivocally limited to one instance.

All of the publications, patents and patent applications cited in this application are herein incorporated by reference in their entirety to the same extent as if the disclosure of each individual publication, patent application or patent was specifically and individually indicated to be incorporated by reference in its entirety.

This written description uses examples to disclose the invention, including the best mode, and also to enable any person skilled in the art to make and use the invention. Many modifications of the exemplary embodiments of the invention disclosed above will readily occur to those skilled in the art. Accordingly, the invention is to be construed as including all structure and methods that fall within the scope of the appended claims. Unless otherwise specified, the recitation of a genus of elements, materials or other components, from which an individual component or mixture of components can be selected, is intended to include all possible subgeneric combinations of the listed components and mixtures thereof.

The invention illustratively disclosed herein suitably may be practiced in the absence of any element which is not specifically disclosed herein.

It should be noted that only the components relevant to the disclosure are shown in the figures, and that many other components normally part of an integrated process unit for making one or more alkylate products are not shown for simplicity.

EXAMPLES

Example 1

Ionic Liquid Catalyst Comprising Anhydrous Metal Halide

Various ionic liquid catalysts made of metal halides such as $AlCl_3$, $AlBr_3$, $GaCl_3$, $GaBr_3$, $InCl_3$, and InBr3 could be used for the processes of this disclosure. N-butylpyridinium chloroaluminate ($C_5H_5NC_4H_9Al_2Cl_7$) ionic liquid catalyst is the ionic liquid catalyst used for the examples described herein. The ionic liquid catalyst had the following composition:

| | |
|---|---|
| Wt % Al | 12.4 |
| Wt % Cl | 56.5 |
| Wt % C | 24.6 |
| Wt % H | 3.2 |
| Wt % N | 3.3 |

Examples 2 and 3

Alkylation of Isobutylene and Isobutane to Make Alkylate Gasoline

Alkylation of isobutylene with isobutane was performed in a continuously stirred tank reactor (CSTR) using chemical grade (>99%) isobutylene and isobutane. A mixture having a molar ratio of 9:1 of isobutane and isobutylene was fed to the alkylation reactor while vigorously stirring. The ionic liquid catalyst described in Example 1 was fed to the alkylation reactor via a second inlet port targeting to occupy 5 vol % in the alkylation reactor. A small amount of n-butyl chloride was added to the alkylation reactor to produce anhydrous HCl gas. The average residence time (combined volume of feeds and catalyst) in the alkylation reactor was about 5 minutes. The outlet pressure was maintained at 100 psig (689 kPa) and the alkylation reactor temperature was maintained either at 95° F. (35° C.) or 80° F. (26.7° C.) using an internal cooling coil immersed in the CSTR alkylation reactor.

The alkylation reactor effluent was separated with a coalescing separator into a hydrocarbon phase and an ionic liquid catalyst phase. The hydrocarbon phase was then distilled on-line using three distillation columns to separate the alkylation reactor effluent into multiple streams: a C3 stream, a nC4 stream, a iC4 stream, and an alkylate gasoline stream. The isobutane stream was recycled back to the alkylation reactor. The alkylate gasoline was analyzed for detailed hydrocarbon composition using gas chromatography. The operating conditions and results of these examples are summarized in Table 1.

TABLE 1

Continuous Alkylation of Isobutane and Isobutylene

| Example Number | Example 2 | Example 3 |
|---|---|---|
| Ionic Liquid (IL) Catalyst | BupyAl$_2$Cl$_7$ | BupyAl$_2$Cl$_7$ |
| Temperature, ° C. | 35 | 27 |
| Ionic liquid catalyst volume, vol % | 5.3 | 5.3 |
| RPM of alkylation reactor stirring | 1600 | 1600 |
| Residence time of reactant, min. | 5.2 | 5.2 |
| External I/O ratio, molar | 9.0 | 9.0 |
| Olefin conversion, wt % | 100 | 100 |

TABLE 1-continued

Continuous Alkylation of Isobutane and Isobutylene

| Example Number | Example 2 | Example 3 |
|---|---|---|
| Alkylate yield, bbl alkylate/bbl olefin | 1.84 | 1.81 |
| $C_{5+}$ Gasoline Composition | | |
| $C_5$ | 4.5 | 4.4 |
| $C_6$ | 6.3 | 6.3 |
| $C_7$ | 7.5 | 7.1 |
| $C_8$ | 62.7 | 61.2 |
| $C_9$ | 10.0 | 9.1 |
| $C_{10+}$ | 9.0 | 11.9 |
| Sum | 100.0 | 100.0 |
| $C_8$ Product Isomer Distribution, wt % | | |
| % tri-Me-pentane/total C8 | 84.7 | 90.4 |
| % Di-Me-hexane/total C8 | 14.2 | 9.1 |
| % Me-Heptane/total C8 | 1.1 | 0.5 |
| % n-Octane/total C8 | 0.0 | 0.0 |
| Sum | 100.0 | 100.0 |

Example 4

Product Properties of Alkylate Gasoline from Isobutylene and Isobutane Alkylation Using Ionic Liquid Catalyst The alkylate gasoline product samples from Examples 2 and 3 were analyzed and the product property data are summarized in Table 2. The average density, average molecular weight, and RVP were calculated based on the gas chromatography composition data.

TABLE 2

Product Properties of Alkylate Gasoline from Isobutane and Isobutylene Alkylation

| Alkylate Source | Example 2 | Example 3 |
|---|---|---|
| Average density, g/ml at 15° C. | 0.70 | 0.70 |
| Average molecular weight, g/mole (calculated) | 113 | 114 |
| Average RVP, psi (calculated) | 3.2 | 3.2 |
| Research Octane Number (RON) | 95.0 | 97.0 |
| Motor Octane Number (MON) | 92.4 | 92.9 |
| (RON + MON)/2 | 93.7 | 95.0 |
| Distillation, D86, ° F. | | |
| IBP | 91 | 80 |
| T-50 | 222 | 224 |
| FBP | 392 | 405 |
| Residual olefins, wt % | <0.1 | <0.1 |
| Sulfur, wppm | <2 | <2 |

The alkylate gasoline samples from isobutane and isobutylene had excellent gasoline properties. The samples had RONs exceeding 95. They were both clean-burning alkylate gasoline with no detectible sulfur, aromatics, or residual olefins. Both of these alkylate gasoline samples had a low average RVP of 3.2 psi. These examples clearly showed that excellent quality alkylate gasoline from alkylation of isobutane and isobutylene using an ionic liquid catalyst can be produced. The mixture of the isobutane and isobutylene fed to the alkylation reactor, as shown in Examples 2 through 4, can be produced from isomerization of n-butane to isobutane, followed by partial dehydrogenation of the isobutane in accordance with the processes and integrated process unit of the present disclosure.

Pure isobutane is readily obtained from a natural gas feedstock, such as from a natural gas liquid stream. The isobutane feed from a natural gas feedstock can be sent to the dehydrogenation reactor directly to form a mixture of isobutylene and isobutane, and then the mixture is sent to the alkylation reactor in accordance with the processes and integrated process unit of the present disclosure.

Example 5

Alkylation of $C_3/C_4$ Olefin with Isobutane to Make Alkylate Jet Fuel

This example used a model feed of FCC olefins as the feed source to make a jet fuel. A blend of feeds to an alkylation reactor was made in this example to model what would be similarly, but more directly, obtained by the partial hydrogenation of natural gas liquid. The blend of feeds in this example comprised a mixed $C_3/C_4$ olefin feed of FCC olefins and refinery grade isobutane/n-butane. However, a mixture of one or more olefins and one or more unconverted paraffins produced instead from the natural gas dehydrogenation according to the process of this disclosure will produce a jet fuel with similar product properties shown in this example.

Alkylation of the mixed $C_3/C_4$ olefin feed with a refinery grade isobutane/n-butane feed was performed in a nozzle loop alkylation reactor, in which a recirculation pump and a nozzle provided intense mixing of the feeds (reactants) with the ionic liquid catalyst described in Example 1. The combined feeds and the catalyst mixture had about 6 minutes of total residence time in the nozzle loop alkylation reactor, which also included an external heat exchanger.

The mixed $C_3/C_4$ olefin feed was from a fluid catalytic cracking (FCC) process and the refinery grade isobutane/n-butane feed mixture was from a butane isomerization process. A combined mixture of the mixed $C_3/C_4$ olefin feed and the refinery grade isobutane/n-butane feed mixture had a molar ratio of 4:1 of isobutane and olefin. This combined mixture was fed to the nozzle loop alkylation reactor. A similar mixture of $C_3/C_4$ olefin feed with n-butane would be made by the dehydrogenation of a $C_3$-$C_4$ natural gas liquid, which provides process simplification compared to using a feed from a FCC process.

The ionic liquid catalyst was fed to a recirculating reactor loop pump suction and targeted to occupy about 4 vol % in the nozzle loop alkylation reactor. A small amount of n-butyl chloride was added to the feed to the nozzle loop alkylation reactor to produce anhydrous HCl gas in situ. The outlet pressure on the nozzle loop alkylation reactor was maintained at 160 psig (1103 kPa) and the alkylation reactor temperature was maintained at 95° F. (35° C.) using the external heat exchanger.

The nozzle loop alkylation reactor effluent was separated with a coalescing separator into a hydrocarbon phase and an ionic liquid catalyst phase. The hydrocarbon phase was then distilled on-line using three distillation columns which separated the nozzle loop alkylation reactor effluent into multiple streams: a C3 stream, a nC4 stream, a iC4 stream, and an alkylate product stream. The isobutane stream was recycled back to the nozzle loop alkylation reactor. The operating conditions and yields from these Examples are summarized in Table 3.

TABLE 3

Continuous Alkylation Process to Produce
Alkylate Gasoline and Jet Fuel

| Example Number | Example 5 |
|---|---|
| Ionic Liquid (IL) Catalyst | BupyAl$_2$Cl$_7$ |
| Temperature, ° C. | 35 |
| Ionic liquid catalyst volume, vol % | 4 |
| Residence time of reactants, min. | 6 |
| External I/O ratio, molar | 4.0 |
| Olefin conversion, wt % | 100 |
| Alkylate yield, bbl alkylate/bbl olefin | 1.60 |
| Vol % Yield | |
| IBF - 250° F. Fraction (light gasoline) | 65 |
| 250° F. - FBP Fraction (jet fuel) | 35 |
| Sum | 100.0 |

This example showed that the selectivity of the alkylate products was changed by adjusting the process conditions. The lowering of the molar ratio of the isoparaffin to the olefin in the alkylation reactor from 9:1 to 4:1 increased the yield of the hydrocarbons with a higher boiling range. The alkylation process using an ionic liquid catalyst made alkylate middle distillate fuels (i.e., alkylate jet fuel or alkylate diesel fuel) effectively by adjusting the process conditions. By lowering the isobutane to olefin ratio (I/O) to 4, the boiling range of the alkylate products was shifted higher towards making heavier alkylate products compared to the earlier examples.

This example that produced the alkylate jet fuel in good yield used C$_3$/C$_4$ mixed olefin feed. This embodiment of the process may be referred to as a distillate-mode alkylation process. With olefin feeds having higher carbons numbers, such as C$_5$ or C$_6$ olefin feeds, the alkylate products would have a further increased amount of hydrocarbons boiling in the middle distillate boiling range, such as the jet fuel boiling range and the diesel fuel boiling range.

Examples 6 and 7

Product Properties of Alkylate Gasoline and Alkylate Jet Fuel from the Distillate-Mode Alkylation Process Using Ionic Liquid Catalyst The whole alkylate product from Example 5 was distillated in a lab to split the product into two fractions. The 250° F.$^-$ fraction (Example 6) was analyzed for its properties as a gasoline blending component (light alkylate gasoline). The 250° F.$^+$ fraction (Example 7) was analyzed for its properties as a middle distillate blending component (i.e., jet fuel or diesel fuel). The product properties of these two fractions are summarized in Tables 4 and 5.

TABLE 4

Product Properties of Alkylate Gasoline from Distillate-
Mode Alkylation Using Ionic Liquid Catalyst

| Properties of Light Gasoline Fraction | | Example 6 |
|---|---|---|
| 250° F.$^-$ Fraction (Light Gasoline) | D86, ° F. | |
| | IBP | 92 |
| | 10 wt % | 134 |
| | 50 wt % | 192 |
| | 90 wt % | 224 |
| | FBP | 258 |
| | RVP, psi | 8.65 |
| | RON | 91.9 |

TABLE 4-continued

Product Properties of Alkylate Gasoline from Distillate-
Mode Alkylation Using Ionic Liquid Catalyst

| Properties of Light Gasoline Fraction | | Example 6 |
|---|---|---|
| | MON | 89.1 |
| | Specific Gravity | 0.68 |
| | Sulfur, wppm | <5 |
| | Cl, wppm (XRF) | 2.0 |

TABLE 5

Product Properties of Alkylate Jet Fuel from Distillate-
Mode Alkylation Using Ionic Liquid Catalyst

| Properties of Distillate Fraction | | Example 7 |
|---|---|---|
| 250° F.$^+$ Fraction (Jet Fuel or Diesel Fuel) | SIMDIST, ° F. | |
| | IBP | 235 |
| | 10 wt % | 254 |
| | 50 wt % | 334 |
| | 90 wt % | 453 |
| | 95 wt % | 502 |
| | FBP | 610 |
| | Flash Point, ° C. | 27.0 |
| | Cloud Point, ° C. | <−60 |
| | Pour Point, ° C. | <−60 |
| | Freeze Point, ° C. | <−60 |
| | Specific Gravity | 0.75 |
| | Sulfur, wppm | <5 |
| | Br Number, g Br/100 g | 0.42 |
| | Smoke Point, mm | 43 |
| | Cl, wppm (XRF) | 1.4 |
| | API at 23° C. | 57.8 |
| | Cetane Index | 55.0 |
| | 6 × 6 Assay | |
| | Paraffin, LV % | 98.4 |
| | Naphthene, LV % | 1.3 |
| | Aromatics, LV % | 0.3 |
| | Aniline Point, ° F. | 183.2 |

Both the light alkylate gasoline and the alkylate middle distillate products had low sulfur (less than 5 wppm) and low chloride (2 wppm or less). The light alkylate gasoline, Example 6, had an excellent RON of 91.9 and had very low sulfur and chloride impurities.

The alkylate jet fuel product, Example 7, was fully saturated with a very low Br number of 0.42 and it was non-cloudy, completely transparent, and had no detectable color when viewed by the naked eye. Composition analysis by 6×6 Assay showed that the alkylate jet fuel product was predominantly comprised of colorless isoparaffins with low aromatics and olefins. The jet fuel fraction exhibited excellent cold flow properties as demonstrated by the cloud point, pour point and freeze point, which were all below the measurable limits of the tests. With the low aromatics content, the alkylate jet fuel showed an excellent smoke point of 43 mm. Impurities were all very low, demonstrated by the low sulfur and low chloride.

It is claimed:

1. A process for making one or more alkylate products, comprising:

a. dehydrogenating a natural gas feedstock comprising saturated hydrocarbons in a dehydrogenation reactor to produce a mixture comprising one or more olefins and one or more unconverted paraffins, wherein the one or more olefins is at least 60 wt % of one or more isopentenes;

b. without further purification or modification other than mixing with isopentane, sending the mixture mixed with isopentane to a single alkylation reactor that is not thermally coupled with the dehydrogenation reactor; and c. alkylating the one or more olefins with isopentane in the single alkylation reactor, using an ionic liquid catalyst, to produce the one or more alkylate products; wherein the one or more alkylate products comprises an alkylate middle distillate with a smoke point of 35 or higher, a freeze point of −40° C. or lower, a Bromine number less than 2, and a sulfur level of 10 wppm or less.

2. The process of claim 1, wherein the natural gas feedstock comprises paraffins in the range of from C2 to C6 paraffins.

3. The process of claim 1, wherein the mixture comprises from 30 to 80 wt % of the one or more unconverted paraffins.

4. The process of claim 1, wherein a molar ratio of the isopentane to the one or more olefins in the single alkylation reactor is from 4:1 to 12:1.

5. The process of claim 1, wherein a molar ratio of the isopentane to the one or more olefins in the single alkylation reactor is adjusted to change a boiling range of the one or more alkylate products.

6. The process of claim 1, wherein dehydrogenating conditions are adjusted depending on the one or more unconverted paraffins that were originally present in the natural gas feedstock, in order to control a dehydrogenation conversion of the natural gas feedstock.

7. The process of claim 1, wherein dehydrogenating conditions include a pressure from 0 to 100 psig, and a temperature from 400° C. to 900° C.

8. The process of claim 1, wherein the dehydrogenating is performed with a dehydrogenation catalyst comprising $Pt/Al_2O_3$, $Cr/Al_2O_3$, Pt/C or a combination thereof.

9. The process of claim 1, additionally comprising maintaining an overall alkylation activity of the ionic liquid catalyst by separating a used ionic liquid catalyst from an effluent of the single alkylation reactor, regenerating a portion of the used ionic liquid catalyst, and returning both a regenerated ionic liquid catalyst from the portion of the used ionic liquid catalyst and the used ionic liquid catalyst remaining after the separating to the single alkylation reactor.

10. The process of claim 1, wherein a co-catalyst comprising a chloride is added to the ionic liquid catalyst.

11. The process of claim 1, wherein the natural gas feedstock is produced by a hydraulic fracturing.

12. The process of claim 1, additionally comprising isomerizing the natural gas feedstock prior to the dehydrogenating, wherein the isomerizing converts some n-pentane in the natural gas feedstock to produce the isopentane that is subsequently alkylated in the single alkylation reactor.

* * * * *